US008748847B2

(12) United States Patent
Sohn et al.

(10) Patent No.: US 8,748,847 B2
(45) Date of Patent: Jun. 10, 2014

(54) METHOD OF MANUFACTURING WHITE LIGHT EMITTING DEVICE (LED) AND APPARATUS MEASURING PHOSPHOR FILM

(71) Applicant: Samsung Electronics Co., Ltd., Suwon-si (KR)

(72) Inventors: Jong Rak Sohn, Hwaseong-si (KR); Seul Gee Lee, Gyeonggi-do (KR); Chul Soo Yoon, Gyeonggi-do (KR); Chang Bun Yoon, Gyeonggi-do (KR); Min Jung Park, Gyeonggi-do (KR); Sang Hoon Ahn, Gyeonggi-do (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 0 days.

(21) Appl. No.: 13/723,855

(22) Filed: Dec. 21, 2012

(65) Prior Publication Data

US 2013/0161534 A1    Jun. 27, 2013

(30) Foreign Application Priority Data

Dec. 23, 2011  (KR) ........................ 10-2011-0141188
Mar. 27, 2012  (KR) ........................ 10-2012-0030951

(51) Int. Cl.
*G01N 21/64*  (2006.01)

(52) U.S. Cl.
USPC ....................................................... 250/458.1

(58) Field of Classification Search
USPC ....................................................... 250/458.1
See application file for complete search history.

(56) References Cited

U.S. PATENT DOCUMENTS

| 7,256,057 | B2 | 8/2007 | Schardt et al. | |
| 8,227,758 | B2 * | 7/2012 | Bechtel et al. | 250/361 R |
| 8,324,001 | B2 * | 12/2012 | Kim | 438/29 |

FOREIGN PATENT DOCUMENTS

| JP | 2000-035363 | 2/2000 |
| JP | 2004-119743 | 4/2004 |
| JP | 2009-224656 | 10/2009 |
| KR | 1990-0008253 | 6/1990 |
| KR | 1020110007705 | 1/2011 |

* cited by examiner

*Primary Examiner* — Kiho Kim
(74) *Attorney, Agent, or Firm* — F. Chau & Associates, LLC

(57) ABSTRACT

A method of manufacturing a white light emitting device includes dividing a phosphor sheet into phosphor film units to be applied to individual light emitting diode (LED) devices, measuring light conversion characteristics of the respective phosphor film units, classifying the phosphor film units of the phosphor sheet into a plurality of groups according to measurement results of the light conversion characteristics and combining the phosphor film units classified into the plurality of groups and an LED device having predetermined light characteristics so as to obtain target color characteristics.

20 Claims, 9 Drawing Sheets

METHOD OF MANUFACTURING WHITE LIGHT EMITTING DEVICE (LED) AND APPARATUS MEASURING PHOSPHOR FILM

CROSS-REFERENCE TO RELATED APPLICATIONS

This application claims priority to Korean Patent Application No. 10-2011-0141188 filed on Dec. 23, 2011, and Application No. 10-2012-0030951 filed on Mar. 27, 2012, the disclosures of which are each hereby incorporated by reference herein in their entireties.

TECHNICAL FIELD

The present disclosure relates to a method of manufacturing a white light emitting device, and more particularly, to a method of manufacturing a white light emitting device including a phosphor film and a phosphor film measuring apparatus capable of being used therefor.

DISCUSSION OF THE RELATED ART

A light emitting diode (hereinafter, referred to as an "LED") is a semiconductor device converting electrical energy into optical energy and configured of a compound semiconductor emitting light having a particular wavelength, according to an energy band gap. LEDs have come into widespread use in back light units (BLUs) for display devices such as, for example, optical communications or mobile display devices, computer monitors, or the like, for liquid crystal displays (LCDs), and in general illumination devices.

Similarly to a general white light emitting diode package, to provide white light, a wavelength conversion unit suitable therefor may be employed therein. Such a wavelength conversion unit may be manufactured using, for example, a phosphor with an LED chip or a wafer through a well-known process such as dispensing or printing at a package level or a wafer level, or may be provided by pre-manufacturing a phosphor in a phosphor film sheet and then bonding the manufactured phosphor film to an LED chip or a wafer.

However, even in a case in which a light emitting device is manufactured through a single process, as white light has color difference properties according to a manufacturing process and characteristics of a conversion in a phosphor layer, and according to products, a defect such as irregular color scattering may occur.

Further, in some cases, light emitting diode packages may emit white light deviating from the range of conditions of target color properties to be required, thereby resulting in defective light emitting diode packages and decreased production yields.

SUMMARY OF INVENTION

An exemplary embodiment of the present invention provides a method of manufacturing a light emitting device and an apparatus for measuring a phosphor film, capable of improving color scattering or precisely controlling color properties by increasing reliability in measuring light conversion characteristics of a phosphor film.

According to an exemplary embodiment of the present invention, there is provided a method of manufacturing a white light emitting device, the method including: dividing a phosphor sheet into phosphor film units to be applied to individual light emitting diode (LED) devices, measuring light conversion characteristics of the respective phosphor film units, classifying the phosphor film units of the phosphor sheet into a plurality of groups according to measurement results of the light conversion characteristics, and combining the phosphor film units classified into the plurality of groups and an LED device having predetermined light characteristics so as to obtain target color characteristics.

The measuring of the light conversion characteristics may include: adjusting a beam size of a reference light source by using an optical system, irradiating the beam adjusted with respect to the size to the respective phosphor film units, and detecting light converted by the irradiated beam.

In this case, the adjusted beam size may be smaller than an area of the phosphor film unit.

A detecting unit used in the detecting may be disposed on a position opposite to a surface of the phosphor film unit to which the beam of the reference light source is irradiated, based on the measured phosphor film unit. The detecting unit used in the detecting may be disposed on the surface of the phosphor film unit to which the beam of the reference light source is irradiated.

The reference light source may be ultraviolet rays or a blue light source.

The dividing of the phosphor sheet into the phosphor film units may include adhering the phosphor sheet to an adhesive sheet, and cutting the phosphor sheet into the phosphor film units. The adhesive sheet may be a light transmission sheet.

The method may further include individually separating the cut phosphor film units from the phosphor sheet and loading the separated phosphor film units on a position for measurement of the light conversion characteristics, before measuring the light conversion characteristics.

Unlike the case above, the method may further include loading the phosphor sheet on the position for the measurement of the light conversion characteristics, before measuring the light conversion characteristics, and the measuring of the light conversion characteristics may include moving the phosphor sheet such that the respective phosphor film units are disposed on the position for the measurement of the light conversion characteristics.

The classifying of the phosphor film units into the plurality of groups may include individually unloading the measured phosphor film units so as to be disposed on different regions according to the measured light conversion characteristics.

The method may further include cutting the phosphor sheet into the phosphor film units after the measuring of the light conversion characteristics, and the classifying of the phosphor film units into the plurality of groups may include classifying the respective phosphor film units by separating the respective phosphor film units from the phosphor sheet so as to be disposed on different regions according to the measured light conversion characteristics.

The LED device may be an LED chip or LED package. Meanwhile, the light conversion characteristics may include color coordinates, and light characteristics of the LED device may include at least one of a peak wavelength and a light output.

According to an exemplary embodiment of the present invention, there is provided an apparatus measuring a phosphor film, including: a reference light source emitting light beam having a predetermined wavelength, a beam adjusting optical system configured to guide the light beam emitted from the reference light source to be irradiated to a phosphor film as a measurement target and configured to control a beam spot size of the light beam to have a size smaller than an area of a phosphor film unit to be applied to an individual LED device on a measurement position of the phosphor film, a detecting unit configured to detect light converted from the light irradiated to the phosphor film and a light conversion characteristics measuring unit configured to measure light conversion characteristics of the detected light.

The detecting unit may be disposed on a position opposite to a surface of the phosphor film to which the light beam is irradiated. The detecting unit may be disposed on the surface of the phosphor film to which the light beam is irradiated.

The phosphor film as the measurement target may be a phosphor sheet divided into a plurality of phosphor film units, and the apparatus may further include a phosphor film moving unit configured to move the phosphor sheet so as to be disposed on the measurement position.

The phosphor film as the measurement target may be the phosphor film unit separated from the phosphor sheet, and the apparatus may further include a loading unit configured to separate the phosphor film unit from a phosphor sheet and load the separated phosphor film unit on the measurement position.

The apparatus may further include an unloading unit configured to separately unload the measured phosphor film units to be disposed on different regions according to the measured light conversion characteristics.

In accordance with an exemplary embodiment of the present invention, an apparatus measuring a phosphor film is provided.
The apparatus includes a reference light source configured to emit a light beam having a predetermined wavelength, a beam adjusting optical system configured to guide the light beam emitted from the reference light source to be irradiated to a phosphor film as a measurement target and configured to control a beam spot size of the light beam to have a size smaller than an area of a phosphor film unit to be applied to an individual LED device on a measurement position of the phosphor film, and a detecting unit including an integrating sphere configured to detect light converted from the light beam irradiated to the phosphor film. The integrating sphere includes an incident window, an inner reflective side surface and a side light window, and the integrating sphere is configured such that the converted light introduced through the incident window thereof is repetitively diffused and reflected by the inner reflective side surface and is emitted through the side light window.

The apparatus further includes a light conversion characteristics measuring unit connected to the detecting unit and configured to measure light conversion characteristics of the detected light and a transporting unit configured to move the phosphor film in a horizontal direction so as to be disposed on a measurement position.

BRIEF DESCRIPTION OF THE DRAWINGS

Exemplary embodiments of the present invention will be more clearly understood from the following detailed description taken in conjunction with the accompanying drawings, in which.

DETAILED DESCRIPTION OF EXEMPLARY EMBODIMENTS

Figure 1:
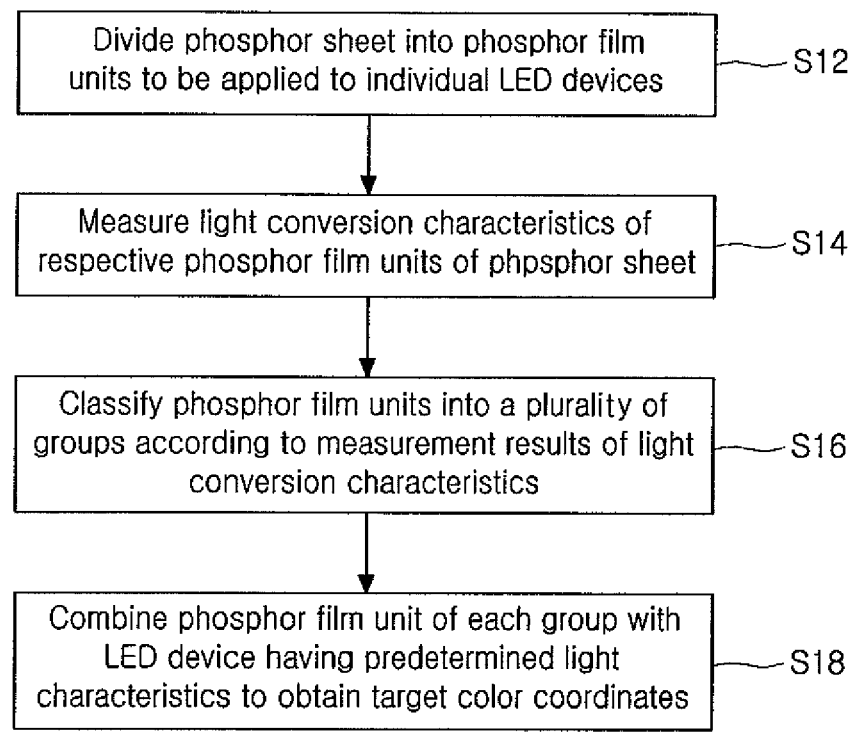
FIG. 1 is a flowchart illustrating a method of manufacturing a white light emitting device according to an embodiment of the present invention.

Hereinafter, exemplary embodiments of the present invention will be described in detail with reference to the accompanying drawings.

In the drawings, the shapes and dimensions of elements may be exaggerated for clarity, and the same reference numerals will be used throughout to designate the same or like elements.

As used herein, the singular forms, "a", "an", and "the" are intended to include plural forms as well, unless the context clearly indicates otherwise.

FIG. 1 is a flowchart illustrating a method of manufacturing a white light emitting device according to an embodiment of the present invention.

For example, as shown in FIG. 1, in a method of manufacturing a white light emitting device according to an embodiment of the present invention, a phosphor sheet may be classified as a "phosphor film unit" in S12.

The term 'phosphor film unit' used here refers to a phosphor film to be applied to an individual LED device. This phosphor film unit may be defined as having different shapes and/or different sizes depending upon devices to which it is applied, and for example, may be directly applied to an LED chip or a specific area of an LED package such as a resin package portion, and may be defined differently according to a shape and a size of an area to be applied.

Classifying the phosphor sheet as a phosphor film unit may include, for example, a visible indication for division or a hypothetical partition. In addition, the classifying of the phosphor sheet as a phosphor film unit may also include a physical process such as, for example, a cutting or a half cutting of the phosphor sheet into a plurality of phosphor film units.

The process of cutting the phosphor sheet into the phosphor film units may be performed, for example, in a state in which the phosphor sheet is adhered to an adhesive tape. In this case, as a position of the phosphor film unit may be maintained in an original position by the adhesive tape, before the cutting of the phosphor sheet, the handling of the phosphor sheet or the respective phosphor film units may be facilitated.

Subsequently, light conversion characteristics of respective phosphor film units on the phosphor sheet may be measured in S14.

The light conversion characteristics of a phosphor film unit on the phosphor sheet measured in S14 may be, for example, a color characteristics value as in color coordinates representatively. In the present embodiment, light conversion characteristics with respect to respective phosphor film units not at an arbitrary point on a phosphor sheet may be measured. The measurement may be performed by, for example, irradiating a beam from a reference light source to an individual phosphor film unit to thus measure light characteristics converted therefrom.

To obtain precise light conversion characteristics information with respect to The phosphor film unit, beam from the reference light source may be controlled to have, for example, a size smaller than the phosphor film unit. For example, to control the beam size, a beam control optical system for light collection may be provided between a reference light source and a phosphor film unit. As such, even in a case in which a beam size is relatively small so as to independently measure respective phosphor film units, a beam area may be, for example, about 10% or greater of an area of a phosphor film unit to increase evaluation reliability of the phosphor film unit.

Next, the phosphor film unit of the phosphor sheet may be classified into a plurality of groups according to measurement results of the light conversion characteristics in S16.

For example, this classification process may be performed by defining chromaticity regions represented by color coordinates in a plurality of groups and designating the respective phosphor film units to respective groups divided by the chromaticity regions according to the measured color coordinates. Here, the respective groups divided according to the chromaticity regions may be "bins", and the classification process as described above may be "binning".

Figure 7:
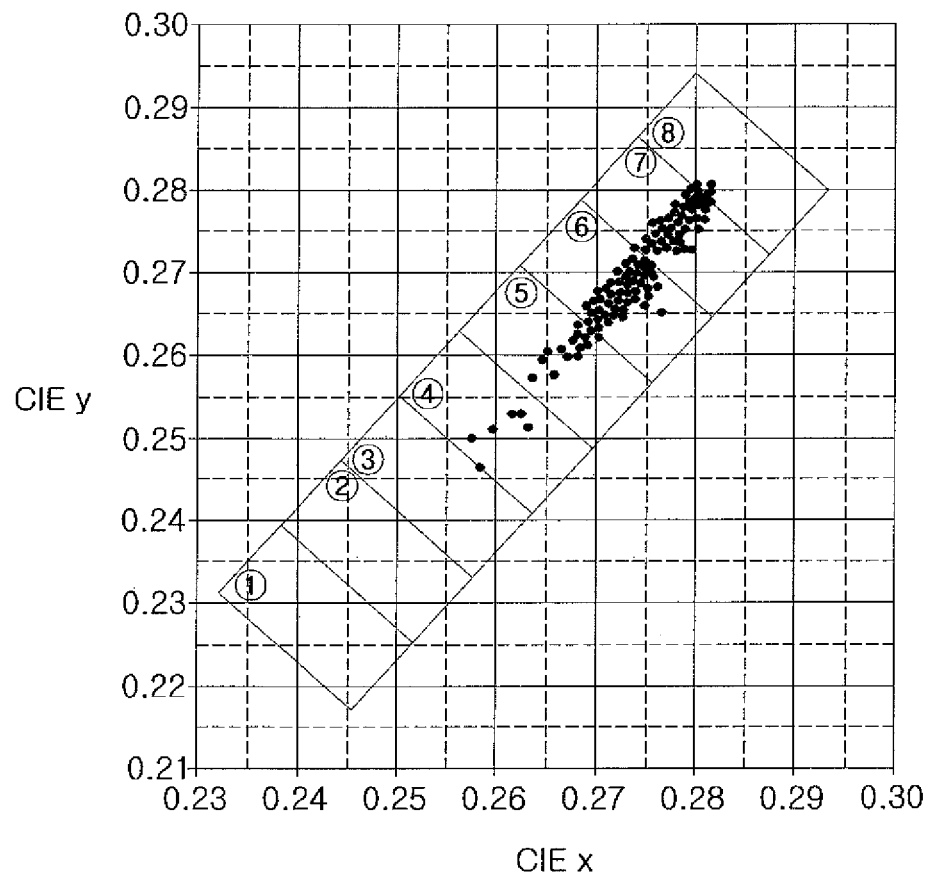
FIG. 7 shows CIE 1931 chromaticity coordinates illustrating phosphor film classification results in a method of manufacturing a white light emitting device according to an embodiment of the present embodiment.

The plurality of phosphor film units obtained from a single phosphor sheet, as well as the phosphor film units obtained in the plurality of phosphor sheets during a single process, may also have some degrees of deviation in the measured light conversion characteristics with respect to FIG. 7.

Unlike the present embodiment, in the case of performing the measurement per each phosphor sheet unit by measuring an arbitrary point on the phosphor sheet, deviations represented in the phosphor film unit may be neglected, and as a result, it may be difficult to expect precise chromaticity control in a final white light emitting device.

As in the present embodiment, as the respective phosphor film units may be measured and classified as predetermined groups, bad influence, for example, color scattering, according to the deviations in the phosphor film unit may be alleviated. For example, in the next process S18, the respective groups of phosphor film units may be combined with LED devices having light characteristics suitable therefor to thus manufacture a white light emitting device having target color characteristics.

To this end, light characteristics of the respective LED devices may also be measured and classified in advance. The light characteristics of the LED devices may be characteristic values such as those in a peak wavelength and a light output. Target color characteristics may be represented by a region specified by color coordinates. The plurality of groups defined as predetermined sections represented by the characteristic values as described above may be set and the LED devices may be classified as respective groups in advance.

The phosphor film units classified in the process described above may, for example, be respectively matched with specific groups of the LED devices so as to satisfy a target color characteristics condition. Correlation for this matching may be obtained through experimentations using samples prepared in advance.

For example, a change in color coordinates of final white light may be confirmed by changing at least one of a peak wavelength and an output from an LED device combined with light color coordinates converted with respect to a reference light source of the phosphor film unit, and a characteristic condition of the LED device satisfying a target color coordinate region required in the final white light may be detected. Consequently, the correlation between characteristics for obtaining the target color coordinate region may be secured in actual matching. A detailed description thereof will be provided below with reference to FIG. 8.

Figure 2:
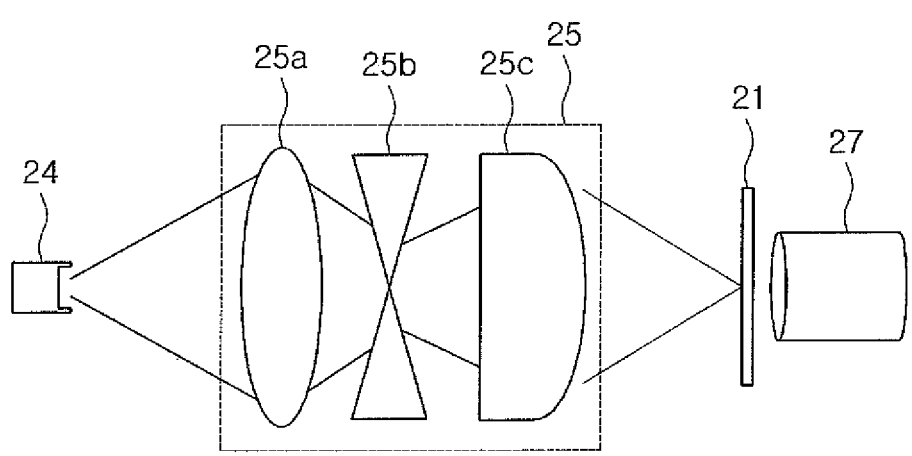
FIG. 2 schematically illustrates an apparatus measuring a phosphor film according to an embodiment of the present invention.

An apparatus measuring a phosphor film according to an embodiment of the present invention will be provided with reference to FIG. 2. The apparatus measuring a phosphor film described in connection with FIG. 2 may be useful for the above-described method of manufacturing a white light emitting device.

FIG. 2 schematically illustrates an apparatus measuring a phosphor film according to an embodiment of the present invention.

A phosphor film measuring apparatus 20 shown in FIG. 2 may include, for example, a reference light source 24 emitting light beams having a predetermined wavelength, and an optical system 25 guiding the light beams from the reference light source so as to emit light to a phosphor film 21 as a target measurement object.

The reference light source 24 may be, for example, an ultraviolet or a blue light source as a short-wavelength light source emitting light having a specific wavelength. For example, the reference light source 24 may be a well-known type of light source such as an LED light source or a halogen light source.

In addition, the phosphor film measuring apparatus 20 may include, for example, a detecting unit 27 detecting light converted by being emitted to the phosphor film 21. The detecting unit 27 may be connected to a light conversion characteristics measuring unit measuring conversion characteristics of the detected converted light.

The phosphor film 21 as the targeted measurement object may be, for example, a phosphor sheet classified as a phosphor film unit, and may be an individual phosphor film unit separated from a phosphor sheet. Even in a case in which the object to be handled is a phosphor sheet itself, one of the plurality of phosphor film units divided on the phosphor sheet may be disposed, for example, at a single measurement position.

Figure 3A:
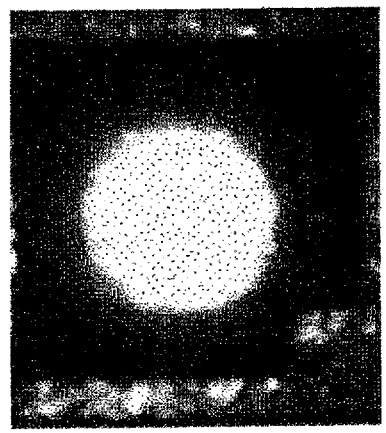
FIGS. 3A and 3B are an image and a schematic view illustrating a relationship between a phosphor film and a beam size according to an embodiment of the present invention.
Figure 3B:
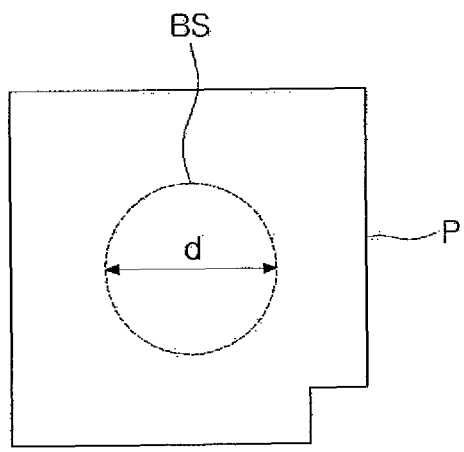

As such, in the phosphor film measuring apparatus 20, there may be a need to control a beam spot size to be reduced at the measurement position to measure the phosphor film unit to be applied to an individual LED device. FIG. 3A is an image illustrating such an actual example, and FIG. 3B is a schematic view illustrating a contour of a phosphor film unit P and light beam BS in the image of FIG. 3A. As shown in FIGS. 3A and 3B, when the emitted light beam BS is controlled to be reduced to a small size d so as to be disposed within the phosphor film unit P, converted light obtained by only being transmitted through a phosphor film unit (P) region may be effectively measured.

To control the beam size, the optical system 25 may be used as a beam adjusting optical system controlling a spot size of the light beam to be emitted to the phosphor film unit so as to have a spot size required therein. The beam adjusting optical system is illustrated to include, for example, a plurality of lens 25a, 25b and 25c arrayed in line on a light axis as shown in FIG. 2, but exemplary embodiments of the present invention are not limited thereto and may have an optical system having well-known, various light collecting structures.

In the present embodiment, the detecting unit 27 may be disposed, for example, on a position opposite to a surface to which the beam is emitted, based on the phosphor film unit 21. That is, the phosphor film measuring apparatus 20 may have, for example, an array in which light converted by penetrating the phosphor film 21 is received.

The phosphor film measuring apparatus according to an embodiment of the present invention may be implemented, for example, in the form having a different array from that shown in FIG. 2. For example, a phosphor film measuring apparatus 40 is shown in FIG. 4 according to an embodiment of the present invention.

Figure 4:
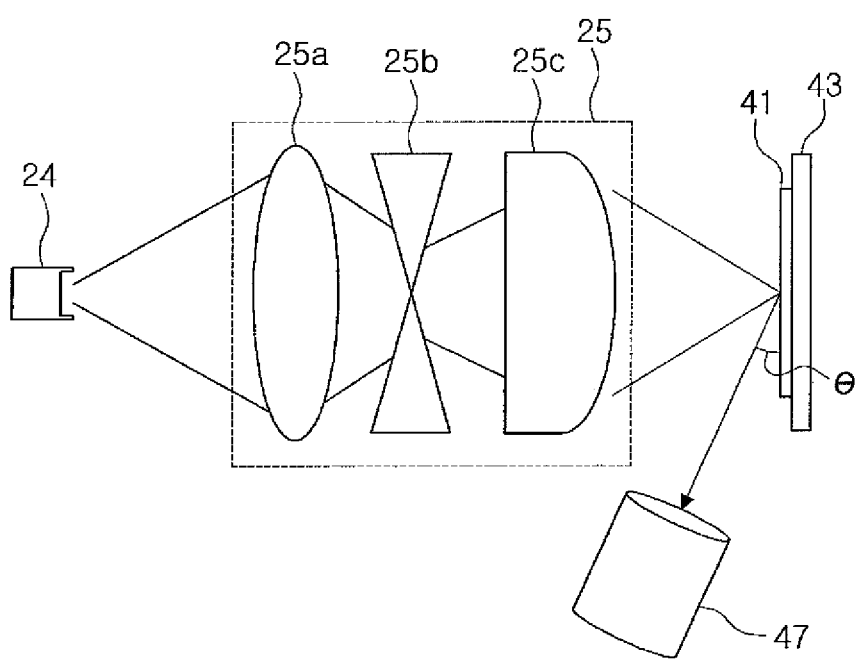
FIG. 4 is a schematic view of a phosphor film measuring apparatus according to an embodiment of the present invention.

The phosphor film measuring apparatus 40 shown in FIG. 4 has a structure similar to that of the previously-described phosphor film measuring apparatus 20, but a detecting unit 47 may be disposed on a surface to which the light beam is emitted, based on a phosphor film 41.

In the present embodiment, a reflective plate 43 may, for example, be disposed on a surface of the phosphor film 41 opposite to a surface thereof to which light is irradiated, such that the converted light may be irradiated on a beam irradiation surface. The detecting unit 47 may be disposed in, for example, a position inclined at a predetermined angle (θ), based on the beam irradiation surface of the phosphor film 41 so as to avoid interference with the emitted beam. For example, the inclination angle (θ) of the detecting unit 47 may be about 30 degrees or less.

In the method of manufacturing a white light emitting apparatus according to an embodiment of the present invention, a phosphor film measuring apparatus according to an embodiment of the present invention may be varied in various forms and implemented due to a difference in schemes of dealing with a phosphor film unit as a measured target, together with measuring and classification methods. A description thereof will be provided with reference to various examples of a phosphor film measuring apparatus shown in FIGS. 5 and 6.

Figure 5:
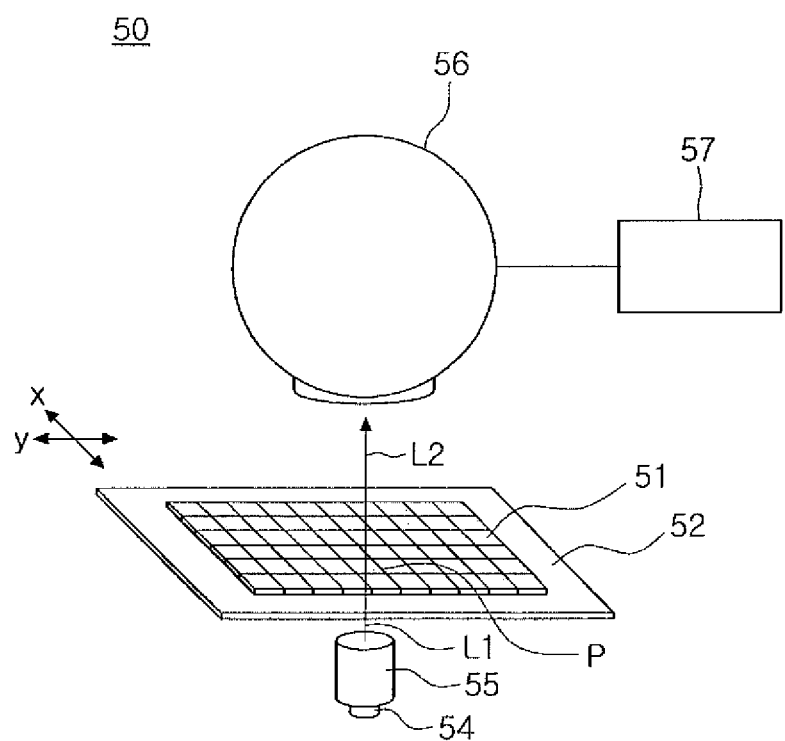
FIGS. 5 and 6 are schematic views illustrating various examples of a phosphor film measuring apparatus with respect to a difference in handling a phosphor film according to an embodiment of the present invention.
Figure 6:
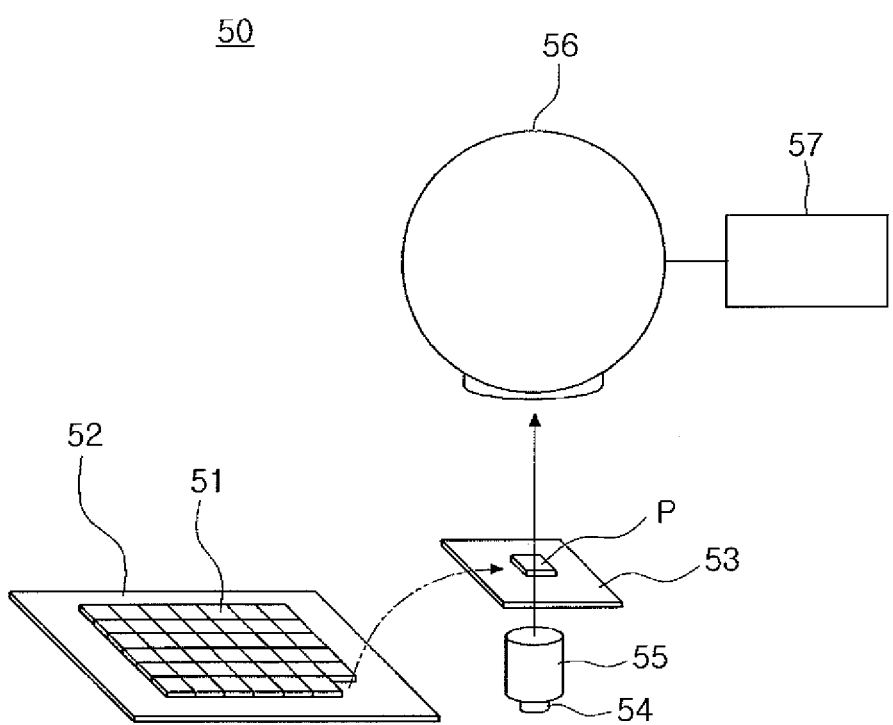

A phosphor film measuring apparatus 50 shown in FIGS. 5 and 6 may include, for example, a reference light source 54 emitting beam L1 having a predetermined wavelength and an optical system 55 guiding the beam L1 from the reference light source 54. In addition, the phosphor film measuring apparatus 50 may include, for example, a detecting unit 56 collecting converted light L2 thereto, and a light conversion measuring unit 57 connected to the detecting unit 56 to measure the converted light L2.

The detecting unit 56 may be, for example, an integrating sphere, a spherical photometer, having a structure in which light introduced through an incident window is repetitively diffused and reflected using an inner reflective side surface and is emitted through a side light window as shown in FIGS. 5 and 6.

In connection with respective components employed in the present embodiment, a description contrary thereto will be understood with reference to the description with regard to elements corresponding thereto according to the pre-described apparatuses of FIGS. 2 and 4. In the present embodiment, the detecting unit 56 may be disposed, for example, on a position opposite to a surface of the reference light source 54 from which the beam is emitted, in a similar manner to the form illustrated in FIG. 2.

First, the phosphor film measuring apparatus shown in FIG. 5 may include, for example, a loading unit (not shown) so as to load a phosphor sheet 51 adhered to an adhesive tape 52 on a measurement position before measuring the light conversion characteristics. The loading unit allows the phosphor sheet 51 to move such that each phosphor film unit of the phosphor sheet 51 is disposed on a measurement position, such that light conversion characteristics of each of the phosphor film units may be measured. In this case, although not shown in FIGS. 5 and 6, the phosphor film measuring apparatus 50 may further include, for example, a transporting unit capable of moving the phosphor sheet 51 serving as a measured target in a horizontal direction (x-y) such that respective phosphor film units P may be measured in order.

The phosphor sheet 51 employed in the present embodiment may be, for example, in a state in which it is cut into phosphor film units P, but may only be virtually partitioned into the phosphor film units P in a state in which it is not individually cut, when necessary, such that an individual measurement of the phosphor film units P may be secured. In the latter case, the adhesive tape may not be additionally required.

Unlike the description above, a phosphor film measuring apparatus shown in FIG. 6 may include, for example, a loading unit (not shown) so as to respectively separate the cut phosphor film units P from a phosphor sheet 51 and load the respectively separated phosphor film units P to a measurement position before measuring the light conversion characteristics. In this case, the phosphor film measuring apparatus may include, for example, a separate support 53 to dispose the phosphor film unit P on the measurement position. The support 53 may be formed of, for example, a light transmission material, such that light beams from the reference light source 54 may be transferred thereto.

As in the present embodiment, in a case in which the phosphor film unit P is measured individually, the phosphor film measuring apparatus may include, for example, an unloading unit (not shown) so as to separately unload and dispose the measured phosphor film units P on different regions according to the measured light conversion characteristics. A classification process may be performed through the processes as described above. Here, the loading unit and the unloading unit may, for example, be integrated to serve as a single device. The unloading process in the present embodiment may be applied, for example, in the form shown in FIG. 5 and also in a state in which the phosphor sheet is cut into phosphor film units P.

Hereinafter, a method of measuring and classifying a phosphor film and a matching method with an LED device will be described through embodiments and examples.

EXAMPLES OF MEASUREMENT AND CLASSIFICATION OF PHOSPHOR FILM

Measurement and classification processes with regard to a ceramic phosphor sheet containing a yellow phosphor were performed using a blue LED of about 450 nm as a reference light source as follows.

First, the ceramic phosphor sheet was adhered to a transparent adhesive sheet and was cut into a plurality of phosphor film units to be applied to an LED chip, and color coordinates of converted light from the respective phosphor film units were measured.

As a result, color coordinates of converted light from the respective phosphor film units were shown in CIE 1931 chromaticity coordinates illustrated in FIG. 7. The CIE 1931 chromaticity coordinates illustrated in FIG. 7 had a plurality of bins represented as color regions distributed in a diagonal direction. A color region of each bin was defined as a 4-dot color coordinate region, and the plurality of bins were continuously distributed.

In these bins, to obtain color coordinates of required target white light, light characteristics of an LED device were classified such that they were classified and represented as color coordinate regions required to be matched with each other.

As shown in FIG. 7, a majority of phosphor film units were classified and represented in bin 6 and bin 7, and furthermore, a portion thereof were represented in a relatively wide distribution over bin 4 and bin 8. As such, despite the phosphor film units obtained on a single phosphor sheet, it could be seen that a color coordinate of light obtained when a reference light source having the same light characteristics is used represented a relatively large deviation.

Figure 8:
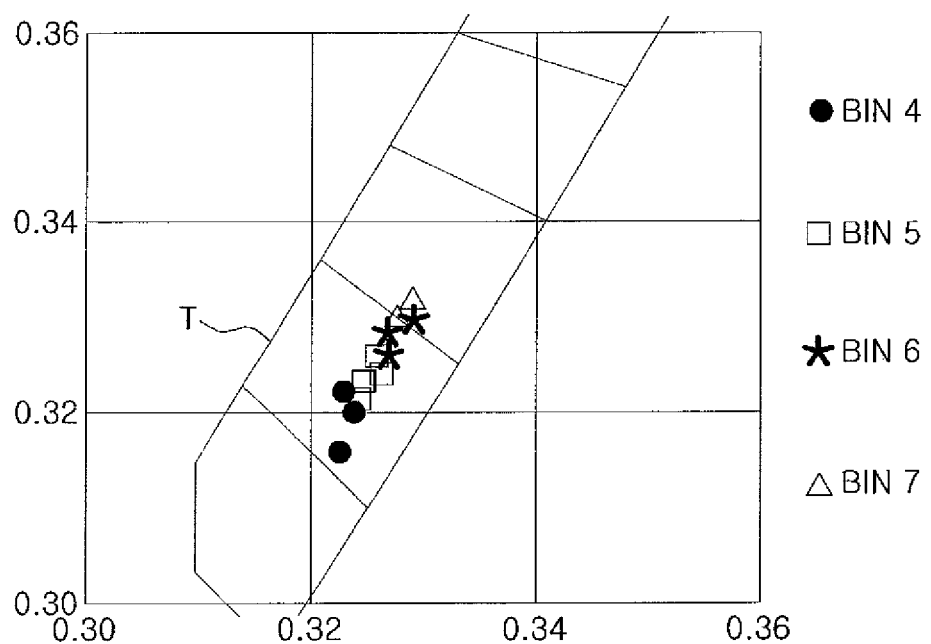
FIG. 8 shows CIE 1931 chromaticity coordinates illustrating color coordinates of white light generated from a white light emitting device manufactured using a phosphor film classified in the method of FIG. 7.

As described above, a portion in the phosphor film unit respectively classified into bin 4 to bin 8 was extracted and applied to a blue LED chip having the same light characteristics (Peak Wavelength: about 455 nm, Light Output: about 143 mW), and color coordinates of white light were represented in the chromaticity coordinates shown in FIG. 8. While bin 5 and bin 6 comparatively satisfied a target color coordinate region, it was confirmed that portions of bin 6 and bin 7 were close to a boundary of the target color coordinate or representing a yellowish-orange deviation.

As shown in FIG. 8, the trend for color scattering similar to that in FIG. 7 in a diagonal direction was represented. That is, it could be confirmed that other light conversion characteristics of the phosphor film unit also relatively greatly affected final white light.

<Matching with LED Device>

As shown in FIG. 8, the phosphor film unit classified into respective groups (bins) represented a difference in light conversion characteristics when actually being combined with a blue LED chip. That is, as described above, while bin 4 and bin 5 comparatively satisfied a target color coordinate region, portions of bin 6 and bin 7 were close to a boundary of the target color coordinate or represented a yellowish-orange deviation. To relieve such a deviation, a combination capable of satisfying a target color region of final white light was detected as follows, by allowing a phosphor film unit of each bin to be combined with a blue LED chip having different light characteristics so as to obtain precise control of final white light. Here, the light characteristics of the blue LED chip were classified by a light output together with a peak wavelength.

TABLE 1

| | Phosphor Film Unit Group | | | | |
|---|---|---|---|---|---|
| | bin 4 | bin 5 | bin 6 | bin 7 | bin 8 |
| Peak Wavelength of Blue LED Chip | 455 nm | 455 nm | 453 nm | 451-453 nm | 447-450 nm |
| Light Output from Blue LED Chip | 140 mW | 143 mW | 143 mW | 144-145 mW | 144-145 mW |

In the case of bin 5, as confirmed in FIG. 8, the target color coordinate region was satisfied by the blue LED chip (Peak Wavelength: about 455 nm, Light Output: about 143 mW), but in the case of bin 4, as it was close to a target color side boundary, the target color coordinate region was stably satisfied using a light output from the blue LED chip, having a relatively low level. In addition, bin 6 and bin 7, representing slight yellowish-orange deviations, were combined with a blue LED chip having a relatively low peak wavelength and slightly high light output, and bin 8, having a highest deviation, was combined with an LED chip having the conditions of a highest peak wavelength and light output.

Figure 9:
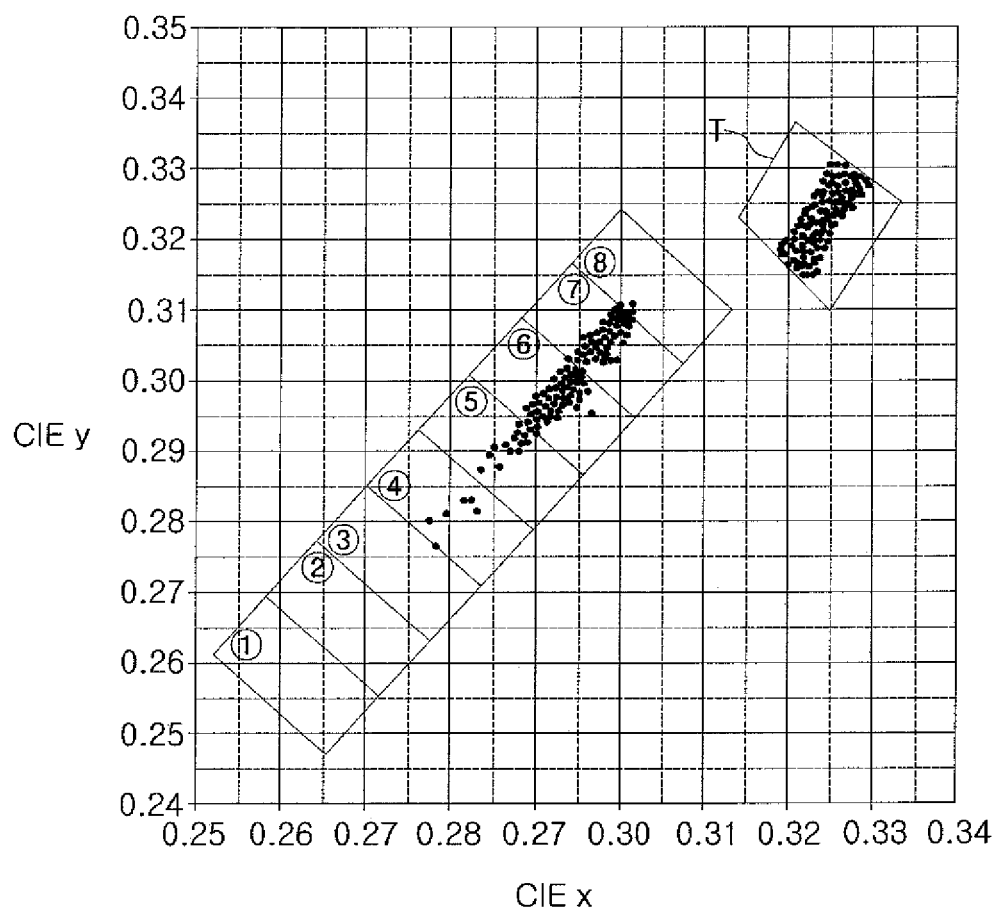
FIG. 9 shows CIE 1931 chromaticity coordinates illustrating color coordinates of white light generated from a white light emitting device manufactured using a phosphor film classified in the method of FIG. 7.

As a result, as shown in FIG. 9, as the phosphor film units having a different color distribution in a relatively wide region, as shown in bin 4 to bin 8, may be increased to become the light emitting device having a color distribution corresponding to target color coordinate regions, color scattering may be increased and a production yield of a light emitting device providing a required color level of white light may be significantly increased.

As such, all color deviations represented in a plurality of phosphor film units obtained from a single phosphor sheet can be considered, as well as those of a plurality of phosphor film units obtained from a plurality of phosphor sheets obtained in a single process, and precise color control may be implemented through a combination with an LED device having light characteristics suitable therefor, such that increased color scattering can be expected.

As set forth above, according to an embodiment of the present invention, light conversion characteristics in a phosphor film may be individually measured and then classified by discriminating between respective units of phosphor films to be applied to individual LED devices, such that color properties may be precisely controlled. In addition, color scattering may be increased relatively greatly so as to satisfy target color coordinates by combining a phosphor film with an LED device having specific light characteristics.

Having described exemplary embodiments of the present invention, it is further noted that it is readily apparent to those of ordinary skill in the art that various modifications may be made without departing from the spirit and scope of the invention which is defined by the metes and bounds of the appended claims.

What is claimed is:

1. A method of manufacturing a white light emitting device, the method comprising:
   dividing a phosphor sheet into phosphor film units to be applied to individual light emitting diode (LED) devices;
   measuring light conversion characteristics of the respective phosphor film units;
   classifying the phosphor film units of the phosphor sheet into a plurality of groups according to measurement results of the light conversion characteristics; and
   combining the phosphor film units classified into the plurality of groups and an LED device having predetermined light characteristics so as to obtain target color characteristics.

2. The method of claim 1, wherein the measuring of the light conversion characteristics includes:
   adjusting a beam size of a reference light source by using an optical system;
   irradiating the beam adjusted with respect to the size to the respective phosphor film units; and
   detecting light converted by the irradiated beam.

3. The method of claim 2, wherein the adjusted beam size is smaller than an area of the phosphor film unit.

4. The method of claim 1, wherein the dividing of the phosphor sheet into the phosphor film units further includes adhering the phosphor sheet to an adhesive sheet, and cutting the phosphor sheet into the phosphor film units.

5. The method of claim 4, further comprising individually separating the cut phosphor film units from the phosphor sheet and loading the separated phosphor film units on a position for measurement of the light conversion characteristics, before measuring the light conversion characteristics.

6. The method of claim 5, wherein the classifying of the phosphor film units into the plurality of groups includes individually unloading the measured phosphor film units so as to be disposed on different regions according to the measured light conversion characteristics.

7. The method of claim 4, further comprising loading the phosphor sheet on the position for the measurement of the light conversion characteristics before measuring the light conversion characteristics, wherein the measuring of the light conversion characteristics includes moving the phosphor sheet such that the respective phosphor film units are disposed on the position for the measurement of the light conversion characteristics.

8. The method of claim 1, further comprising cutting the phosphor sheet into the phosphor film units after the measuring of the light conversion characteristics, wherein the classifying of the phosphor film units into the plurality of groups includes classifying the respective phosphor film units by separating the respective phosphor film units from the phosphor sheet so as to be disposed on different regions according to the measured light conversion characteristics.

9. The method of claim 1, wherein the light conversion characteristics include color coordinates, and light characteristics of the LED device include at least one of a peak wavelength and a light output.

10. An apparatus measuring a phosphor film, comprising:
a reference light source configured to emit a light beam having a predetermined wavelength;
a beam adjusting optical system configured to guide the light beam emitted from the reference light source to be irradiated to a phosphor film as a measurement target and configured to control a beam spot size of the light beam to have a size smaller than an area of a phosphor film unit to be applied to an individual LED device on a measurement position of the phosphor film;
a detecting unit configured to detect light converted from the light beam irradiated to the phosphor film; and
a light conversion characteristics measuring unit configured to measure light conversion characteristics of the detected light.

11. The apparatus of claim 10, wherein the detecting unit is disposed on a position opposite to a surface of the phosphor film to which the light beam is irradiated.

12. The apparatus of claim 10, wherein the detecting unit is disposed on the surface of the phosphor film to which the light beam is irradiated.

13. The apparatus of claim 10, wherein the phosphor film as the measurement target is a phosphor sheet divided into a plurality of phosphor film units, and the apparatus further includes a phosphor film moving unit configured to move the phosphor sheet so as to be disposed on the measurement position.

14. The apparatus of claim 13, further comprising an unloading unit configured to separately unload the measured phosphor film units to be disposed on different regions according to the measured light conversion characteristics.

15. The apparatus of claim 10, wherein the phosphor film as the measurement target is the phosphor film unit separated from a phosphor sheet, and the apparatus further includes a loading unit configured to separate the phosphor film unit from the phosphor sheet and load the separated phosphor film unit on the measurement position.

16. The apparatus of claim 10, wherein the beam adjusting optical system includes a plurality of lens arrayed in a line on a light axis.

17. The apparatus of claim 10, wherein the detecting unit is disposed on a position opposite to a surface to which the light beam is emitted from the phosphor film.

18. The apparatus of claim 10, wherein a reflective plate is disposed on a surface of the phosphor film, and wherein the detecting unit is disposed at a position inclined at a angle of no greater than about 30 degrees with respect to an irradiation surface of the phosphor film.

19. An apparatus measuring a phosphor film, comprising:
a reference light source configured to emit a light beam having a predetermined wavelength;
a beam adjusting optical system configured to guide the light beam emitted from the reference light source to be irradiated to a phosphor film as a measurement target and configured to control a beam spot size of the light beam to have a size smaller than an area of a phosphor film unit to be applied to an individual LED device on a measurement position of the phosphor film;
a detecting unit including an integrating sphere configured to detect light converted from the light beam irradiated to the phosphor film, wherein the integrating sphere includes an incident window, an inner reflective side surface and a side light window, wherein the integrating sphere is configured such that the converted light introduced through the incident window thereof is repetitively diffused and reflected by the inner reflective side surface and is emitted through the side light window; and
a light conversion characteristics measuring unit connected to the detecting unit and configured to measure light conversion characteristics of the detected light; and
a transporting unit configured to move the phosphor film in a horizontal direction so as to be disposed on a measurement position.

20. The apparatus of claim 19, wherein the phosphor film is adhered to an adhesive tape, the apparatus further comprising a separate support configured to receive phosphor film units separated from the phosphor film for measurement thereon.

* * * * *